United States Patent
Yoon et al.

(10) Patent No.: US 9,631,713 B2
(45) Date of Patent: Apr. 25, 2017

(54) DRIVING FORCE TRANSFER DEVICE FOR END-EFFECTOR

(71) Applicants: KOH YOUNG TECHNOLOGY INC., Seoul (KR); INDUSTRY-UNIVERSITY COOPERATION FOUNDATION HANYANG UNIVERSITY ERICA CAMPUS, Ansan-si, Gyeonggi-do (KR)

(72) Inventors: Hyun-Soo Yoon, Ansan-si (KR); Byung-Ju Yi, Bucheon-si (KR)

(73) Assignees: KOH YOUNG TECHNOLOGY INC., Seoul (KR); INDUSTRY-UNIVERSITY COOPERATION FOUNDATION HANYANG UNIVERSITY ERICA CAMPUS, Ansan-si, Gyeonggi-Do (KR)

( * ) Notice: Subject to any disclaimer, the term of this patent is extended or adjusted under 35 U.S.C. 154(b) by 183 days.

(21) Appl. No.: 14/349,576

(22) PCT Filed: Apr. 19, 2013

(86) PCT No.: PCT/KR2013/003350
§ 371 (c)(1),
(2) Date: Jan. 20, 2015

(87) PCT Pub. No.: WO2013/162217
PCT Pub. Date: Oct. 31, 2013

(65) Prior Publication Data
US 2015/0128763 A1    May 14, 2015

(30) Foreign Application Priority Data
Apr. 26, 2012   (KR) .................. 10-2012-0044126

(51) Int. Cl.
*F16H 37/06*    (2006.01)
*F16H 1/20*     (2006.01)
*A61B 34/30*    (2016.01)

(52) U.S. Cl.
CPC ........... *F16H 37/065* (2013.01); *A61B 34/30* (2016.02); *Y10T 74/19051* (2015.01)

(58) Field of Classification Search
CPC ........ F16H 37/065; F16H 1/225; A61B 17/29
(Continued)

(56) References Cited

U.S. PATENT DOCUMENTS

| 5,720,590 A | * | 2/1998 | Hofmeister | B25J 9/107 414/744.2 |
| 6,017,358 A | * | 1/2000 | Yoon | A61B 17/29 600/564 |

(Continued)

FOREIGN PATENT DOCUMENTS

| JP | 07-238996 | 9/1995 |
| KR | 20-0445028 | 6/2009 |

(Continued)

OTHER PUBLICATIONS

Written Opinion of the International Searching Authority for International Application No. PCT/KR2013/003350, dated Jul. 31, 2013.
(Continued)

*Primary Examiner* — Ha D Ho
(74) *Attorney, Agent, or Firm* — Kile Park Reed & Houtteman PLLC

(57) ABSTRACT

A driving force transfer device for an end-effector, the driving force transfer device comprising at least one double shaft member which separately receives driving forces generated from first and second driving means through first and
(Continued)

second power transfer means and transfers the driving forces to an end-effector such that the end-effector has two rotational degrees of freedom.

8 Claims, 4 Drawing Sheets

(58) Field of Classification Search
USPC .............................. 74/665 A, 424.5; 606/205
See application file for complete search history.

(56) References Cited

U.S. PATENT DOCUMENTS

| | | | |
|---|---|---|---|
| 7,476,237 B2* | 1/2009 | Taniguchi | A61B 17/29 |
| | | | 606/205 |
| 8,377,044 B2* | 2/2013 | Coe | A61B 17/00234 |
| | | | 606/1 |
| 8,640,788 B2* | 2/2014 | Dachs, II | A61B 19/2203 |
| | | | 173/164 |
| 9,283,054 B2* | 3/2016 | Morgan | A61B 34/74 |
| 2008/0056856 A1* | 3/2008 | Krupyshev | H01L 21/67196 |
| | | | 414/217 |

FOREIGN PATENT DOCUMENTS

| | | |
|---|---|---|
| KR | 10-0946175 | 3/2010 |
| KR | 10-1234399 | 2/2013 |

OTHER PUBLICATIONS

International Search Report for International Application No. PCTG/KR2013/003350 dated Jul. 31, 2013.

\* cited by examiner

DRIVING FORCE TRANSFER DEVICE FOR END-EFFECTOR

TECHNICAL FIELD

Exemplary embodiments of the present invention relate to a driving force transfer device for an end-effector. More particularly, exemplary embodiments of the present invention relate to a driving force transfer device that transmits power of a driving means to an end-effector.

BACKGROUND ART

In general, laparascopic surgery robot uses driving force transfer device to couple the driving means and an end-effector to receive power from driving means.

Usually, the driving force transfer device installs power transfer device such as gear or pulley to a shaft to drive the end-effector by rotating the shaft through the received power from the driving means.

As conventional general driving force transfer device comprises a single shaft with a single rotational degree of freedom, there is a problem that a size of the driving force transfer device increases as it requires to install shaft as a number of rotational degree of freedom needed. And as a result, a size of an end-effector increases. In addition, manufacturing cost and maintenance/repairing cost, and assembling steps are increased as a number of parts increase.

DISCLOSURE

Technical Problem

Therefore, the object of the present invention is to provide a driving force transfer device for end-effector with two rotational degrees of freedom using single shaft member.

Technical Solution

In one embodiment of the present invention, a driving force transfer device includes at least one double shaft member receiving each of driving forces that are generated from a first and second driving means and transferred from a first and second power transfer means, such that an end-effector has two rotational degrees of freedom.

In one embodiment, the double shaft member is formed in a hollow shape and is connected to the end-effector and includes a first rotation shaft that receives a driving force through the first power transfer means generated from the first driving means, and a second rotation shaft that receives a driving force through the second power transfer means generated from the second driving means. The second rotation shaft is coupled to the end-effector and rotatably inserted to the inside of the first rotation shaft such that it is protruded to an outside of an end portion of the first rotation shaft.

Herein, the first rotation shaft includes a first end-effector connection part coupled to the end-effector and the second rotation shaft rotatably inserted to the inside of the first end-effector connection part, and a first shaft part coupled to the first end-effector connection part and the second rotation shaft rotatably inserted to the inside of the first shaft part, and receiving a driving force through the first power transfer means generated from the first driving means.

Also, the second rotation shaft includes a second end-effector connection part coupled to the end-effector and rotatably inserted to the inside of the first rotation shaft, and a second shaft part coupled to the second end-effector connection part and an end portion of the second end-effector connection part being rotatably inserted to the inside of the first rotation shaft such that it is protruded to an outside of the end portion of the first rotation shaft, and the end portion protruded to the outside of the first rotation shaft receiving a driving force through the second power transfer means generated from the second driving means.

Herein, the first and second power transfer means may be a gear.

More preferably, the first and second power transfer means may be a helical gear.

Alternatively, the first and second power transfer means may be pulleys that are installed on each of the first and second rotation shaft and connected to the first and second driving means.

Herein, the power transfer means may be a wire.

Advantageous Effects

Thus, according to an embodiment of the present invention, a driving force transfer device for end-effector transfers each of driving force generated from a first and second driving means using single double shaft member to an end-effector separately, such that the end-effector has two rotational degrees of freedom. Therefore, it is possible to manufacture an end-effector in compact size by reducing whole size of driving force transfer device of end-effector to less than half compared to the conventional driving force transfer device when rotational degrees of freedom is increased in designing an end-effector with plural a rotational degrees of freedom. And it is effective to reduce production cost and maintenance/repairing cost as well as assembling steps by reducing number of using parts.

MODE FOR INVENTION

Figure 1:
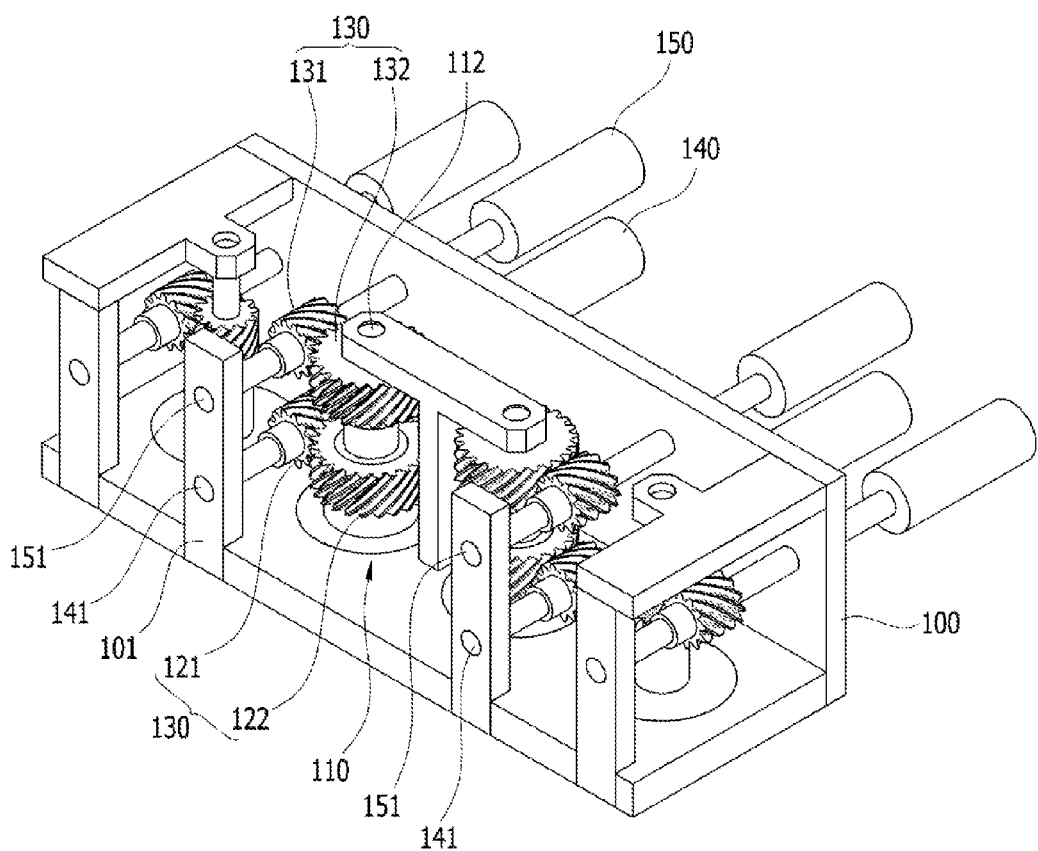
FIG. 1 is a drawing showing a driving force transfer device for end-effector according to a first embodiment of the present invention.

The present invention is described more fully hereinafter with reference to the accompanying drawings, in which example embodiments of the present invention are shown. The present invention may, however, be embodied in many different forms and should not be construed as limited to the example embodiments set forth herein. Rather, these example embodiments are provided so that this disclosure will be thorough and complete, and will fully convey the scope of the present invention to those skilled in the art. In the drawings, the sizes and relative sizes of layers and regions may be exaggerated for clarity.

It will be understood that, although the terms first, second, third etc. may be used herein to describe various elements, components, regions, layers and/or sections, these elements, components, and/or sections should not be limited by these terms. These terms are only used to distinguish one element, component, region, layer or section from another region, layer or section. Thus, a first element, component, or section discussed below could be termed a second element, component, or section without departing from the teachings of the present invention.

The terminology used herein is for the purpose of describing particular example embodiments only and is not intended to be limiting of the present invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

For convenience, same numerals are used for identical or similar elements of an apparatus of cutting a tempered substrate and the conventional one.

Hereinafter, with reference to the drawings, preferred embodiments of the present invention will be described in detail.

Embodiment 1

Figure 2:
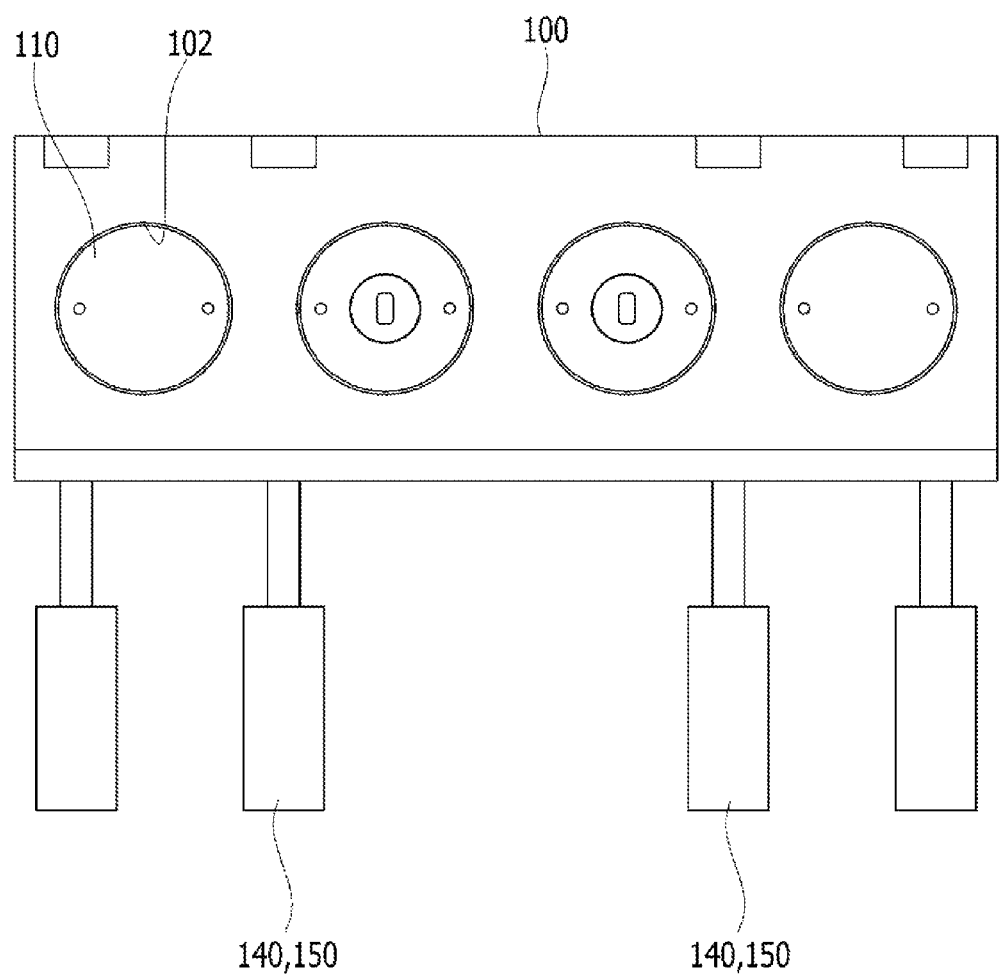
FIG. 2 is a bottom view of FIG. 1.

FIG. 1 is a drawing showing a driving force transfer device for end-effector according to a first embodiment of the present invention, and FIG. 2 is a bottom view of FIG. 1.

Referring to FIGS. 1 and 2, a driving force transfer device according to an embodiment of the present invention comprises a housing 100, at least one double shaft member 110, and first and second power transfer means 120 and 130.

At least one couple of a first and second driving means is installed in one side of the housing 100. Herein, rotation shafts 141 and 151 of the first and second driving means 140 and 150 are inserted to the inside of the housing 100 and passes through one side of the housing 100. And an end portion of the rotation shafts 141 and 151 which are inserted to inside of the housing by passing through one side of the housing 100 of the first and second driving means 140 and 150 is supported by the supporting member installed on another side of the housing 100 in rotatable manner. Herein, couple of the first and second driving means makes a team and is connected to the double shaft member 110.

The at least one double shaft member is disposed above the housing in rotatable manner. In more detail, at least one hole 102 is formed through the bottom of the housing 100, a holding member (not shown) may be installed on the at least one hole 102 to make the double shaft member to rotate. Therefore, the bottom of the double shaft member 110 is externally exposed and coupled to an end-effector (not shown).

Each of the power transfer means 120 and 130 transfers driving force to the double shaft member that is generated from each of the first and second driving means 140 and 150. And the double shaft member receives the driving forces generated from the first and second driving means through the first and second power transfer means, transfers separately the first driving force generated from the first driving means and the second driving force generated from the second driving means to the end-effector and such that the end-effector has two rotational degrees of freedom using single shaft member.

Figure 3:
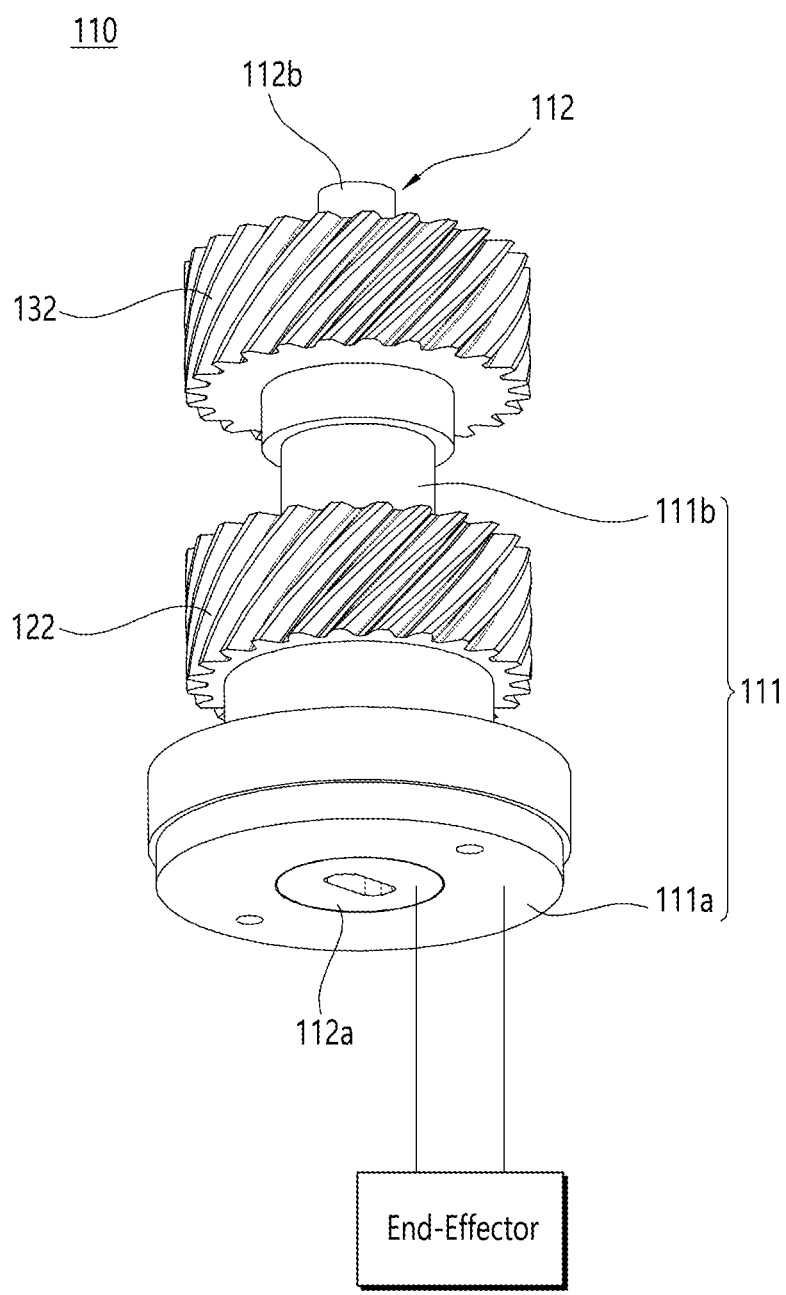
FIG. 3 is a perspective view showing a double shaft member according to the first embodiment of the present invention.

FIG. 3 is a perspective view showing a double shaft member according to the first embodiment of the present invention;

Referring to FIGS. 1-3, the double shaft member includes a first rotation shaft 111 and a second rotation shaft 112.

The first rotation shaft 111 is formed in a hollow shape and coupled to the end-effector (not shown). Also, the first rotation shaft 111 is coupled to the first driving means 140 through the first power transfer means 120. Therefore, the first rotation shaft 111 receives driving force generated from the first driving means through the first power transfer means, in other words, receives rotatory power and transfers it to the end-effector. Herein, the first power transfer means may be a gear. For example, the first power transfer means may be a helical gear. In other words, a first helical part 121 is installed on rotation shaft 141 of the first driving means 140, a second helical part 122 is connected to the first helical part 121 with gear and installed on the first rotation shaft 111 such that rotatory power of the first driving means 140 is transferred to the first rotation shaft 111 through the first and second helical parts 121 and 122, and an end-effector coupled to the first rotation shaft is rotated and has one rotational degree of freedom.

The second rotation shaft 112 is rotatably inserted and coupled to the inside of the first rotation shaft such that it is protruded to an outside of the end portion of the first rotation shaft, and coupled to the end-effector. The second rotation shaft 112 receives driving force generated from the second driving means 150 through the second power transfer means 130, in other words, receives rotatory power and transfers it to the end-effector. For example, the second power transfer means may be a helical gear. In other words, a first helical part 131 is installed on the rotation shaft 151 of the second driving means 150, a second helical part 132 is installed on an end portion of the second rotation shaft 112 which is protruded to the outside of the first rotation shaft 111, and rotatory power of the second driving means 150 is transferred to the second rotation shaft 121 through the first and second helical parts 131 and 132, such that the second rotation shaft is rotated separate to the first rotation shaft 111, and the end-effector coupled to the second rotation shaft 121 is rotated and has another rotational degree of freedom.

Referring to FIGS. 1-3 again, composition of the first and second rotation shaft is described in detail as below.

Referring to FIGS. 1-3, the first rotation shaft 111 includes a first end-effector connecting part 111a and a first shaft part 111b.

The first end-effector connecting part 111a is coupled to end-effector (not shown), and rotatably inserted and coupled to the inside of the second rotation shaft 112. In more detail, the first end-effector connecting part 111a is rotatably installed to a shaft holding member (not shown) which is formed on a hole 102 of the housing 100, and is coupled to the end effector, such that the second rotation shaft 112 is rotatably inserted and coupled to the inside of the first end-effector 111a.

The first shaft part 111b is coupled to the first end-effector connecting part 111a, such that the second rotation shaft 112 is rotatably inserted and coupled to the inside of the first shaft part 111b. Also, the first shaft part 111b receives driving force generated from the first driving means 140 through the first power transfer means 120. In other words, the first shaft part 111b receives driving force generated from the first driving means 140, in other words, rotatory power, by installing a first helical part 121 installed on the first driving means 140 and a second helical part 122 connected with gear to the first helical part 121, and receives rotatory power generated from the first driving means 140.

The second rotation shaft 112 includes a second end-effector connecting part 112a and a second shaft part 112b.

The second end-effector connecting part 112a is coupled to the end-effector, and is rotatably inserted and coupled to the inside of the first rotation shaft 111. In more detail, the second end-effector connecting part 112a is coupled to the end effector by inserting and coupling the second end-effector connecting part 112a to the inside of the first end-effector connecting part 111a in rotatable manner.

The second shaft part 112b is inserted and coupled to the inside of the first rotation shaft 111 in rotatable manner, such that it is coupled to the second end effector connecting part 112a. At this point, the second shaft part 112b is inserted and coupled to the inside of the first shaft 111b such that an end portion of the second shaft part 112b is protruded to an outside of the first shaft part 111b. Meanwhile, the end portion of the second shaft part 112b that is protruded to the outside of the first shaft part 111b receives driving force generated from the second driving means 150 through the second power transfer means 130, in other words, receives rotatory power. In other words, the end portion of the second shaft part 112b that is protruded to the outside of the first shaft part 111b is coupled to a first helical part 131 installed on the second driving means 150 with gear, and as a result a second helical part 132 that receives rotatory power of the second driving means 150 through the first helical part 131 is installed such that it receives driving force generated from the second driving means 150, in other words rotatory power.

Embodiment 2

Figure 4:
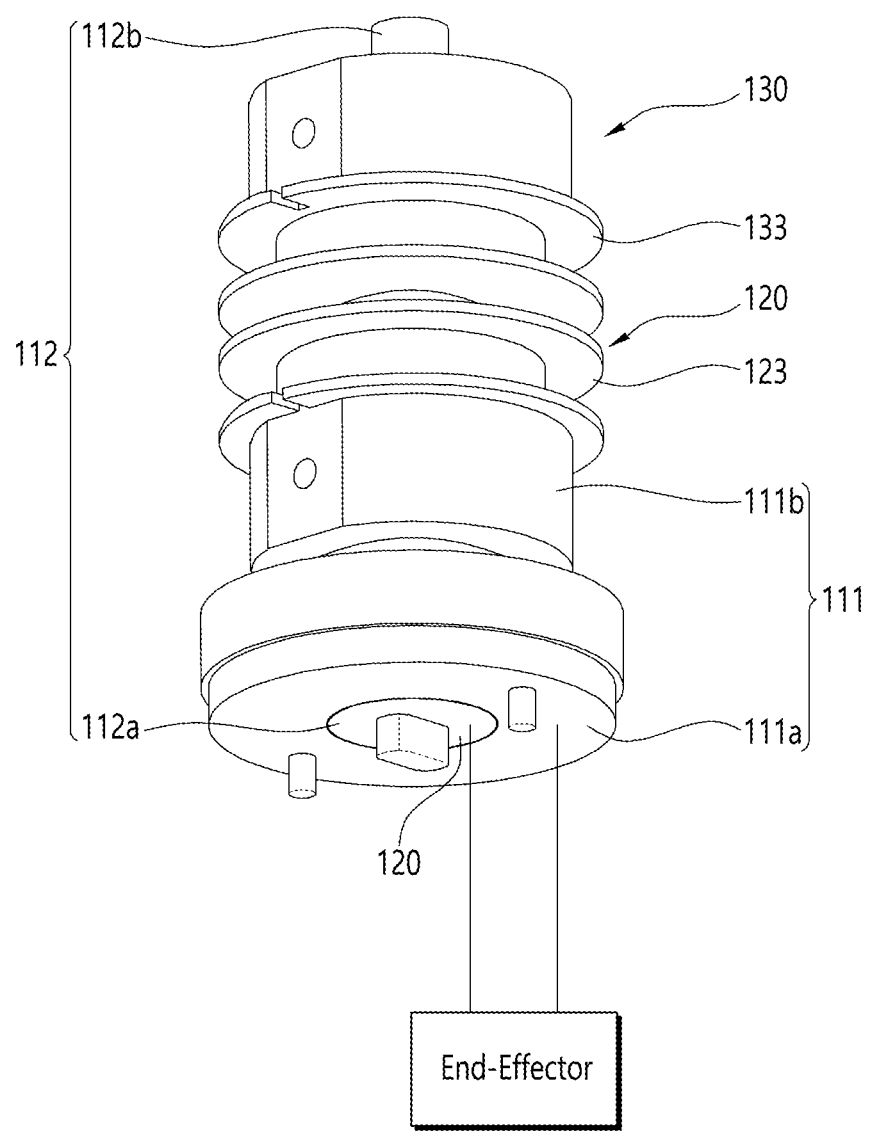
FIG. 4 is a perspective view a double shaft member according to a second embodiment of the present invention.

FIG. 4 is a perspective view a double shaft member according to a second embodiment of the present invention;

According to an embodiment of the present invention, a driving force transfer device is substantially the same as the driving force transfer device according to the first embodiment except that driving force generated from the first and second driving means 140 and 150 is transferred to the double shaft member through the first and second power transfer means 120 and 130. Thus, detailed description of other elements except for the first and second power transfer means 120 and 130 of the driving force transfer device for end-effector will be omitted, and the same reference numerals are used for the same elements to the first embodiment.

Referring FIG. 4, the first power transfer means 120 of driving force transfer device for end-effector may be a pulley that is installed on the first rotation shaft 111 and the first driving means (140, refer to FIG. 1) and is coupled by a power transfer member (not shown), such that driving force generated from the first driving means is transferred to the first rotation shaft 111 through the power transfer member. For example, the first power transfer means 120 includes a first driven pulley 123 installed on the first rotation shaft 111, a first driving pulley (not shown) installed on the first driving means 140, and a first power transfer member (not shown) that couples the first driven 123 pulley and the first driving pulley to transfer rotatory power of the first driving means to the first rotation shaft 111.

The second power transfer means 130 may be a pulley that is installed on the second rotation shaft 112 and the second driving means (150, refer to FIG. 1) and is coupled by the power transfer member (not shown) such that driving force generated from the second driving means is transferred to the second rotation shaft 112 through the power transfer member. For example, the second power transfer means 130 includes a second driven pulley 133 installed on the second rotation shaft 112, a second driving pulley (not shown) installed on the second driving means, and a second power transfer member (not shown) that couples the second driven 133 pulley and the second driving pulley to transfer rotatory power of the second driving means to the second rotation shaft 112. Herein, the second driven pulley 133 is installed on an end portion of the second rotation shaft 112 that is protruded to an outside of the first rotation shaft 111.

As described above, according to an embodiment of the present invention, driving force transfer device for an end-effector transfers each of driving force generated form first and second driving means 140 150 through single double shaft member 110 to an end-effector separately, such that the driving force transfer device has two rotational degrees of freedom.

Therefore, it is possible to manufacture an end-effector in compact size by reducing whole size of a driving force transfer device of end-effector to less than half compared to the conventional driving force transfer device when rotational degrees of freedom is increased in designing an end-effector with plural a rotational degrees of freedom. And it is effective to reduce production cost and maintenance/repairing cost as well as assembling steps by reducing number of using parts.

It will be apparent to those skilled in the art that various modifications and variation can be made in the present invention without departing from the spirit or scope of the invention. Thus, it is intended that the present invention cover the modifications and variations of this invention provided they come within the scope of the appended claims and their equivalents.

The invention claimed is:

1. A driving force transfer device for end-effector comprising:
   first and second driving means generating driving forces;
   first and second power transfer means transferring the driving forces; and
   at least one double shaft member that separately receives the driving forces generated from the first and second driving means through the first and second power transfer means, and transfers the driving forces to an end-effector having two rotational degrees of freedom,
   wherein the double shaft member comprises:
      a first rotation shaft formed in a hollow shape and coupled to the end-effector, the first rotation shaft receiving the driving force generated from the first driving means through the first power transfer means; and
      a second rotation shaft rotatably inserted and coupled to the inside of the first rotation shaft such that an end portion of the second rotation shaft is protruded to an outside of the first rotation shaft and coupled to the end-effector, the second rotation shaft receiving the driving force generated from die second driving means through the second power transfer means, and
   wherein each of the first and second power transfer means is gear.

2. The device of claim 1, wherein the first rotation shaft comprising:
   a first end-effector connecting part coupled to the end-effector, the second rotation shaft being rotatably inserted and coupled to the inside of the first end-effector connecting part; and a first shaft part coupled to the first end-effector connecting part, the second rotation shaft being rotatably inserted and coupled to the inside of the first shaft part, and receiving the driving force generated from the first driving means through the first power transfer means.

3. The device of claim 1, wherein the second rotation shaft comprising:

a second end-effector connecting part coupled to the end-effector, and rotatably inserted and coupled to the inside of the first rotation shaft;

a second shaft part coupled to the second end-effector connecting part, and rotatably inserted and coupled to the inside of the first rotation shaft such that an end portion of the second shaft part is protruded to an outside of the first rotation shaft, the end portion that is protruded to the outside of the first rotation shaft receives the driving force generated from the second driving means through the second power transfer means.

4. The device of claim 1, wherein the first and second power transfer means are helical gear.

5. A driving force transfer device for end-effector comprising:

first and second driving means generating driving forces;

first and second lower transfer means transferring the driving forces; and at least one double shaft member that separately receives the driving forces generated from the first and second driving means through the first and second power transfer means, and transfers the driving forces to an end-effector having two rotational degrees of freedom, wherein the double shaft member comprises:

a first rotation shaft formed in a hollow shape and coupled to the end-effector, the first rotation shaft receiving the driving force generated from the first driving means through the first power transfer means; and a second rotation shaft rotatably inserted and coupled to the inside of the first rotation shaft such that an end portion of the second rotation shaft is protruded to an outside of the first rotation shaft and coupled to the end-effector, the second rotation shaft receiving the driving force generated from the second driving means through the second power transfer means, and wherein the first and second power transfer means are pulleys that are installed on the first and second rotation shaft and the first and second driving means, respectively, and are coupled by a power transfer member.

6. The device of claim 5, wherein the power transfer member is a wire.

7. The device of claim 5, wherein the first rotation shaft comprising:

a first end-effector connecting part coupled to the end-effector, the second rotation shaft being rotatably inserted and coupled to the inside of the first end-effector connecting part; and a first shaft part coupled to the first end-effector connecting part, the second rotation shaft being rotatably inserted and coupled to the inside of the first shaft part, and receiving the driving force generated from the first driving means through the first power transfer means.

8. The device of claim 5, wherein the second rotation shaft comprising:

a second end-effector connecting part coupled to the end-effector, and rotatably inserted and coupled to the inside of the first rotation shaft;

a second shaft part coupled to the second end-effector connecting part, and rotatably inserted and coupled to the inside of the first rotation shaft such that an end portion of the second shaft part is protruded to an outside of the first rotation shaft, the end portion that is protruded to the outside of the first rotation shaft receives the driving force generated from the second driving means through the second power transfer means.

* * * * *